US010064571B2

(12) United States Patent
Burnet

(10) Patent No.: US 10,064,571 B2
(45) Date of Patent: Sep. 4, 2018

(54) METHOD AND APPARATUS FOR DETECTING THE ONSET OF HYPOGLYCAEMIA

(71) Applicant: Medvet Science Pty Ltd, Underdale (AU)

(72) Inventor: Richard Bruce Burnet, Moonta (AU)

(73) Assignee: MEDVET SCIENCE PTY LTD, Underdale (AU)

( * ) Notice: Subject to any disclaimer, the term of this patent is extended or adjusted under 35 U.S.C. 154(b) by 113 days.

(21) Appl. No.: 14/364,493

(22) PCT Filed: Dec. 12, 2012

(86) PCT No.: PCT/AU2012/001516
§ 371 (c)(1),
(2) Date: Jun. 11, 2014

(87) PCT Pub. No.: WO2013/086564
PCT Pub. Date: Jun. 20, 2013

(65) Prior Publication Data
US 2014/0343462 A1 Nov. 20, 2014

(30) Foreign Application Priority Data

Dec. 12, 2011 (AU) ................................ 2011905150

(51) Int. Cl.
*A61B 5/103* (2006.01)
*A61B 5/117* (2016.01)
(Continued)

(52) U.S. Cl.
CPC ........... *A61B 5/1101* (2013.01); *A61B 5/1118* (2013.01); *A61B 5/14532* (2013.01);
(Continued)

(58) Field of Classification Search
CPC . A61B 5/1101; A61B 5/1118; A61B 5/14532; A61B 5/7225; A61B 5/7257;
(Continued)

(56) References Cited

U.S. PATENT DOCUMENTS

| 8,821,418 | B2 * | 9/2014 | Meger | A61B 5/0002 600/595 |
| 8,942,779 | B2 * | 1/2015 | Halperin | A61B 5/4343 600/347 |
| 2006/0260842 | A1 | 11/2006 | Sim et al. | |

FOREIGN PATENT DOCUMENTS

| CN | 1866986 A | 11/2006 |
| CN | 101301202 A | 11/2008 |

(Continued)

OTHER PUBLICATIONS

Extended European Search Report dated Sep. 7, 2015 for EP Patent Application No. 12 856 995.1, 9 pages.
(Continued)

*Primary Examiner* — Devin Henson
(74) *Attorney, Agent, or Firm* — Kilpatrick Townsend & Stockton LLP

(57) ABSTRACT

A method and apparatus for the detection of the onset of hypoglycaemia is described. A portable sensor worn by a subject is used to detect a physiological tremor signal. The tremor signal is analysed over a period of time, and an alarm is generated when a change in the physiological tremor signal indicative of the onset of hypoglycaemia in the subject is detected. A patient or carer can then perform appropriate action, such as performing a finger prick test to determine blood sugar test and treating as required. The portable sensor can be used to detect a tremor signal indicative of the, the onset of hypoglycaemia such as a signal corresponding to a decrease in blood glucose level (BGL) below 5 mmol/l. The portable sensor can use an
(Continued)

accelerometer and may be worn on a limb, such as an arm or leg. The sensor can be used to measure the power of the tremor signal and detect a change, such as an increase in power over time and/or an increase in the rate of change of power over time. Filtering the signal may include filtering signals outside of the range 0-50 Hz, or more specifically 7-15 Hz.

37 Claims, 11 Drawing Sheets

(51) Int. Cl.
*A61B 5/11* (2006.01)
*A61B 5/145* (2006.01)
*A61B 5/00* (2006.01)

(52) U.S. Cl.
CPC .......... *A61B 5/6801* (2013.01); *A61B 5/7282* (2013.01); *A61B 5/746* (2013.01); *A61B 5/681* (2013.01); *A61B 5/6824* (2013.01); *A61B 5/6825* (2013.01); *A61B 5/7257* (2013.01); *A61B 5/7275* (2013.01); *A61B 2562/0219* (2013.01)

(58) Field of Classification Search
CPC ..... A61B 5/7282; A61B 5/746; A61B 5/6801; A61B 5/681; A61B 5/6824; A61B 5/6825; A61B 5/7275

See application file for complete search history.

(56) References Cited

FOREIGN PATENT DOCUMENTS

| | | |
|---|---|---|
| JP | 2008253560 | 10/2008 |
| JP | 2011-220993 A | 11/2011 |
| WO | 2006025055 | 3/2006 |
| WO | 2007052108 | 5/2007 |
| WO | 2007099522 | 9/2007 |
| WO | 2009138976 | 11/2009 |
| WO | 2011/007271 A1 | 1/2011 |
| WO | 2011161672 | 12/2011 |

OTHER PUBLICATIONS

International Search Report PCT/AU2012/001516 dated Feb. 13, 2013.
Written Opinion of the International Searching Authority dated Feb. 13, 2013.
Office Action received in the related Chinese Patent Application No. 201280061111.2, dated May 26, 2016.

\* cited by examiner

METHOD AND APPARATUS FOR DETECTING THE ONSET OF HYPOGLYCAEMIA

PRIORITY DOCUMENTS

The present application is a National Stage Entry of PCT/AU2012/001516, which claims priority from Australian Provisional Patent Application No 2011905150 entitled "DEVICE FOR DETECTING ONSET OF HYPOGLYCAEMIA" and filed on 12 Dec, 2011, the content of which is hereby incorporated by reference in its entirety.

TECHNICAL FIELD

The present invention relates to a method and apparatus for the detection of the onset of hypoglycaemia.

BACKGROUND

Diabetes mellitus is a medical condition where the levels of blood glucose are elevated and if left untreated leads to coma and death. The sufferer has great difficulty in controlling their blood glucose level, typically leaving them in a chronic state of hyperglycaemia, or high blood glucose level. There are two major forms of persistent, and currently incurable, diabetes, type 1 and type 2 diabetes. Type 1 diabetics have lost the ability to produce the hormone insulin due to the destruction of the islets of Langerhans in the pancreas. The reason for the destruction is an autoimmune condition but the trigger for this is unknown. Type 1 diabetics must take regular insulin injections, up to 6 per day, to provide their body with enough insulin to allow the cells of their body to process glucose correctly. Insulin administration, along with careful monitoring of diet and exercise, can allow a diabetic to live a relatively normal life. Type 1 diabetes affects around 140,000 Australians and more than 24 million people worldwide. Approximately 4,400 Australian children have type 1 diabetes, with 800 new cases diagnosed per year. Globally, 430,000 children have type 1 diabetes with 65,000 new cases per year. The annual incidence rate of type 1 diabetes in children is growing at about 3% a year. Type 2 diabetes, which is also known as maturity onset diabetes, is due to a premature failure of the islets to produce adequate insulin levels to control the blood glucose values. It affects about 6 to 8% of the population over 50. Both types suffer the same complications from long standing hyperglycaemia.

Chronic hyperglycaemia can cause a number of long term complications, including blindness, chronic renal failure (it is now the most common cause for long term dialysis), ulceration of the lower limbs which may lead to amputation, heart attacks, stroke and neuropathic disease. To reduce the occurrence, onset and severity of these complications, diabetics are advised to keep their blood glucose level in the normal range. Type 1 diabetics do this by the administration of insulin and careful planning and tracking of food intake and exercise. However, this can (and does) give rise to the risk of hypoglycaemia, where the blood glucose level (BGL) drops too low (ie below about 3 or 3.5 mmol/l). Hypoglycaemia has a number of symptoms, including dizziness, irritability, slurring of speech and sweating. Left untreated, hypoglycaemia can lead to fainting, unconsciousness, fitting and, in some cases, death. During a severe hypoglycaemic episode, the sufferer may also sustain some brain injury which, over a number of attacks, can lead to measurable, permanent brain damage. "Dead in bed" scenario accounts for approximately 6% of all deaths of type 1 diabetics below the age of 40; it is thought that nocturnal hypoglycaemia is the cause.

Type 2 diabetics are initially controlled with diet and oral hypoglycaemic agents but after about 10 years, approximately one half of all sufferers will need to administer insulin to control the blood glucose levels and they can also have hypoglycaemia.

Beyond the medical complications, there is the obvious physical danger that hypoglycaemia poses to sufferers. The threat of unconsciousness while driving or even just walking down the street is a part of everyday life for people dealing with hypoglycaemia. Hypoglycaemia is often unpredictable due to poor dietary habits (missing a meal), excessive exercise and erratic absorption of subcutaneous insulin. As a result, due to the risk of a severe hypoglycaemic event that may result from insulin treatment (or oral hypoglycaemics), many diabetics avoid "tight control" of blood glucose levels, making them more susceptible to the long term effects of both hyperglycaemia and hypoglycaemia.

Whilst the effects of prolonged hypoglycaemia can be significant, simple and effective treatment can be provided by the diabetic themselves if detected early enough, simply by consuming a sugar (or glucose) rich food source (eg a few jellybeans) so as to raise their blood glucose levels.

Whilst there are some symptoms discussed above which may alert a diabetic to the onset of hypoglycaemia (or during a hypoglycaemic event), these are not reliable or always detectable (such as when the diabetic is asleep). Further, over time, approximately 17% of type 1 diabetics develop hypoglycaemia unawareness, where they are unable to detect the onset of hypoglycaemia. The level of hypoglycaemia unawareness increases with the length of time that the sufferer has had diabetes.

Early work in this area was performed by Heller et al. (Influence of Sympathetic Nervous System on Hypoglycaemic Warning Symptoms, *The Lancet*, Aug. 15, 1987, p359-363) who studied the effect of mild insulin-induced hypoglycaemia on symptoms, physiological changes and adrenaline responses in aware diabetics, unaware diabetics and controls. In this study, blood glucose was maintained for 30 minutes at levels of 4.5 mmol/l, 3.2 mmol/l, 2.5 mmol/l and again at 4.5 mmol/l for 30 mins. At each stage, symptom scores, adrenaline levels and physiological parameters including tremor, sweating, heart rate and blood pressure reaction time were measured. Statistically significant changes in all three groups was only observed for reaction time and adrenaline levels when blood glucose dropped to the most extreme level of 2.5 mmol/l. Significant changes in symptom score, tremor, blood pressure and sweat levels were only detected for the controls and aware diabetics when blood glucose dropped to the most extreme level of 2.5 mmol/l. Onset of hypoglycaemia (based on statistically significant change from 4.5 mmol/l to 3.2 mmol/l) was only detected for aware diabetics and controls in relation to adrenaline levels, and by all three groups based on reaction times. This work indicated that onset could not be predicted via tremor.

Due to such difficulties, devices for detecting the onset of, or actual hypoglycaemia, have concentrated on continuous monitoring of blood glucose levels. Such devices are typically expensive and invasive, requiring insertion of a needle under the user's skin to contact either blood or interstitial fluid in order to record blood glucose levels. Some non-invasive devices have been developed which attempt to indirectly detect the onset of hypoglycaemia by measuring a combination of physiological parameters, such as skin temperature, resistance (eg sweat levels), respiration rate, heart rate, restlessness or tremors. However, such devices have been limited to use whilst the patient is asleep due to sensitivity, portability and reliability issues.

Thus, there is a need for an inexpensive and reliable wearable device for detecting and alerting the user of the onset of hypoglycaemia, or at least to provide such persons with a useful alternative.

SUMMARY

According to a first aspect of the present invention, there is provided a method for alerting a subject of the onset of hypoglycaemia, the method including the steps of:

i) receiving a physiological tremor signal from a portable sensor worn by a subject;

ii) analysing the physiological tremor signal over a first period of time; and iii) generating an alarm when a change in the physiological tremor signal indicative of the onset of hypoglycaemia in the subject is detected.

In one aspect, the portable sensor comprises an accelerometer.

In one aspect, the onset of hypoglycaemia corresponds to a decrease in blood glucose level (BGL) below 5 mmol/l.

In one aspect, the change is relative to a predetermined baseline. A predetermined baseline may be predetermined for the subject from a calibration process.

Alternatively, the change may be relative to a dynamic threshold determined from analysing the physiological tremor signal over a second period of time, the second period of time preceding the first period of time.

The step of analysing the physiological tremor signal over a first period of time may comprise:

filtering the signal from the sensor;

calculating the power spectrum of the signal at a plurality of time points in the first period of time to obtain a plurality of power measurements; and detecting a change in the plurality of power measurements over the first period of time; or otherwise comprise:

filtering the signal from the sensor;

calculating the power spectrum of the signal continuously in the first period of time to obtain a continuous power measurement(s); and detecting a change in the power measurement(s) over the first period of time.

The change may be an increase in power over time and/or an increase in the rate of change of power over time. Filtering the signal may include filtering signals outside of the range 0-50 Hz, or more specifically 7-15 Hz.

According to a second aspect of the present invention, there is provided a wearable apparatus for detecting the onset of hypoglycaemia in a subject, the apparatus including:

a sensor for measuring physiological tremor in a subject;

an analysis module for analysing a physiological tremor signal from the sensor over a first period of time and generating an alarm signal to initiate an alarm to alert the subject when a change in the physiological tremor signal indicative of the onset of hypoglycaemia in the subject is detected.

In one aspect, the sensor comprises an accelerometer.

In one aspect, the analysis module generates an alarm signal to initiate an alarm to alert the subject of the onset of hypoglycaemia upon a decrease in blood glucose level (BGL) to below 5 mmol/l.

In one aspect, the change is relative to a predetermined baseline. A predetermined baseline may be predetermined for the subject from a calibration process.

Alternatively, the change may be relative to a dynamic threshold determined from analysing the physiological tremor signal over a second period of time, the second period of time preceding the first period of time.

The apparatus may comprise an alarm module wherein the alarm module receives the alarm signal and generates an alarm to alert the subject when a change in the physiological tremor signal, indicative of the onset of hypoglycaemia in the subject, is detected.

The present invention may be embodied in the form of a processor readable medium including processor readable instructions to cause a processor to implement the method of the first aspect. Similarly, the present invention may be embodied in the form of an apparatus including a memory and a processor may be provided in which the processor is configured to implement the method of the first aspect.

BRIEF DESCRIPTION OF DRAWINGS

A preferred embodiment of the present invention will be discussed with reference to the accompanying drawings wherein.

In the following description, like reference characters designate like or corresponding parts throughout the figures.

DESCRIPTION OF EMBODIMENTS

Figure 1:
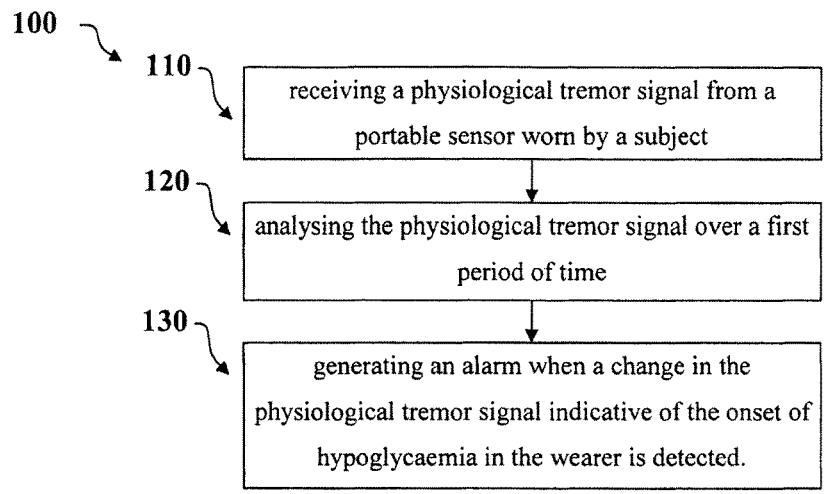
FIG. 1 provides a flowchart of a method for detecting the onset of hypoglycaemia in a subject according to an embodiment of the invention.

It has been discovered that despite early evidence to the contrary, the onset of hypoglycaemia can in fact be detected through analysis of physiological tremor signal from a sensor worn by an individual. Data from laboratory and field trials as described herein show that this signal may be detected both at night, and more importantly, whilst the subject is awake and performing a range of normal day to day activities. Accordingly, a reliable method and a wearable (and thus portable) apparatus (or device) for detecting and alerting the user of the onset of hypoglycaemia can be developed as described herein.

Physiological muscle tremor (also referred to as physiological tremor, or more simply tremor) is defined as a rapid involuntary rhythmic oscillation of a body segment. Physiological tremor is not normally observable, and most individuals are not aware of their own physiological tremor. It can occasionally be observed indirectly such as apparent shaking of the spot from a laser pointer being held by lecturer. In some persons, physiological muscle tremor has larger oscillations, known as "essential tremor" which can then be observed by such persons or others causing social embarrassment and interfering with their occupation. This invention primarily relates to detection of normal physiological muscle tremor in individuals as an indicator of onset of hypoglycaemia, although it would also be suitable for detection of the stronger essential tremor as such an indicator.

The exact cause of physiological tremor is not known, however it is hypothesised that it is the result of an oscillating system of neurons in the central nervous system with a frequency of 8-12 Hz. Due to mechanical effects, the range of physiological tremor varies with the location of measurement, although it is generally between about 0-50 Hz. For example, tremor is typically between about 8-12 Hz when measured at the wrist, 3-5 Hz when measured at the elbow, and 17-30 Hz when measured at the metacarpophalangeal joint.

Walsh (E Geoffrey Walsh (University of Edinburgh) *Physiological Finger Tremor in Medical Students and Others in Handbook of Tremor Disorders,* 1995, Edited by Leslie Findley and William Koller; Marcel Dekker INC, Chapter 5 Pages 63-78) studied finger tremor in a group of medical students and found that tremor was not affected by factors such as thyroid hormone levels, smoking, coffee, alcohol and sex. Tremor amplitude was found to increase (~25%) after exercise, and in pilots when landing planes. The relationship between adrenaline levels and tremor was also studied. Adrenaline is not directly involved in muscle activation, but it is the major component of the "fight or flight" response and has a range of effects which stimulate muscles. The effect of adrenaline levels on tremor were studied using intravenous infusions of adrenaline and isoprenaline, which both increased the amplitude of finger tremor which could then be reduced by beta blockers (ie propranalol). The doses of adrenaline used in these studies were however, significantly higher than typical physiological levels. In subsequent studies by Heller et al. (1987) in which hypoglycaemia was induced in controls and diabetics (both aware and unaware diabetics), it was found that when extreme hypoglycaemia was induced (2.5 mmol/l) there was a significant increase in adrenaline concentrations in all three groups, and a significant increase in tremor in the control and aware diabetics (but not unaware diabetics). No change in tremor was observed during onset of hypoglycaemia (from 4.5 mmol/l to 3.2 mmol/l) although there was a significant change (p<0.05) in adrenaline levels for the control and aware diabetics (but not unaware diabetics).

These previous studies suggest that adrenaline can be considered to be the main stimulus for altering the amplitude of physical tremor.

As these results indicated that onset could not be predicted via muscle tremor, it appears that no further work on studies into the use of finger tremor to predict onset of hypoglycaemia have been performed up until the studies described herein. These further laboratory and field studies have provided new information on the relationship between physical tremor and onset of hypoglycaemia, and in contrast to the earlier study of Heller et al. (1987), have advantageously shown that physiological tremor can indeed be used as predictor of the onset of hypoglycaemia. Further, this signal can be detected during normal daytime activities leading to the development of a wearable, and thus portable, apparatus.

Four studies are now outlined.

The first study was performed to:

1. Identify if a change occurs in the physiological muscle tremor of the arm to hypoglycaemia in insulin requiring diabetic patients (IDDM);
2. Determine if the muscle tremor was similar in hypoglycaemic aware and hypoglycaemic unaware patients;
3. Determine if there was a significant change in muscle tremor that could be used to identify the presence of hypoglycaemia in diabetic patients; and
4. Correlate changes in muscle tremor with adrenaline and noradrenaline levels.

The first study included 18 subjects equally divided into control, hypoglycaemia aware and hypoglycaemia unaware groups. Subjects were seated in a reclined position in a chair and an accelerometer was taped on the index finger of their non-dominant hand. The accelerometer was connected to a laptop computer and analysed by digitising the signal, band pass filtering the signal, Fourier transforming, and then measuring the power of the band pass filtered signal (units $(cm/s^2)^2$). Measurements were taken in a resting position and an elevated position. Symptom scores, pulse rate, blood pressure, adrenaline levels, noradrenaline levels and blood glucose levels (both venous blood and finger prick via a "precision meter") were also monitored.

Blood glucose levels (BGL) were controlled and lowered until BGL had dropped to a value of between 2.4 and 2.8 mmol/l via a finger prick test. Samples were taken every 10 minutes until BGL reached approximately 5 mmol/l and 5 minutes thereafter until completion of the study.

TABLE 1

Details of the subjects

|  | Aware | Unaware | Controls |
|---|---|---|---|
| Sex | 4m, 2f | 3m, 3f | 4m, 2f |
| Age | 45.5 | 49.3 | 45.5 |
| Wt | 82.4 | 83.7 | 69 |
| Height | 172.8 | 174 |  |
| BMI | 27.1 | 26.5 | 24.5 |
| Duration | 20.5 | 29 |  |
| HbA1C | 8.4 | 8.9 |  |

Figure 3:
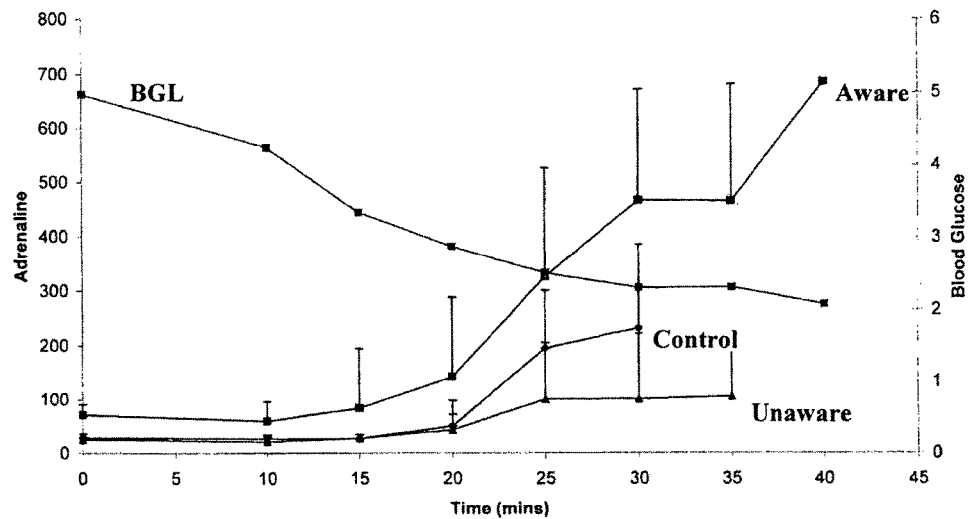
FIG. 3 is a plot of Adrenaline and Blood Glucose Levels (BGL) vs time for control, hypoglycaemic aware and hypoglycaemic unaware groups in a first study described herein.
Figure 4:
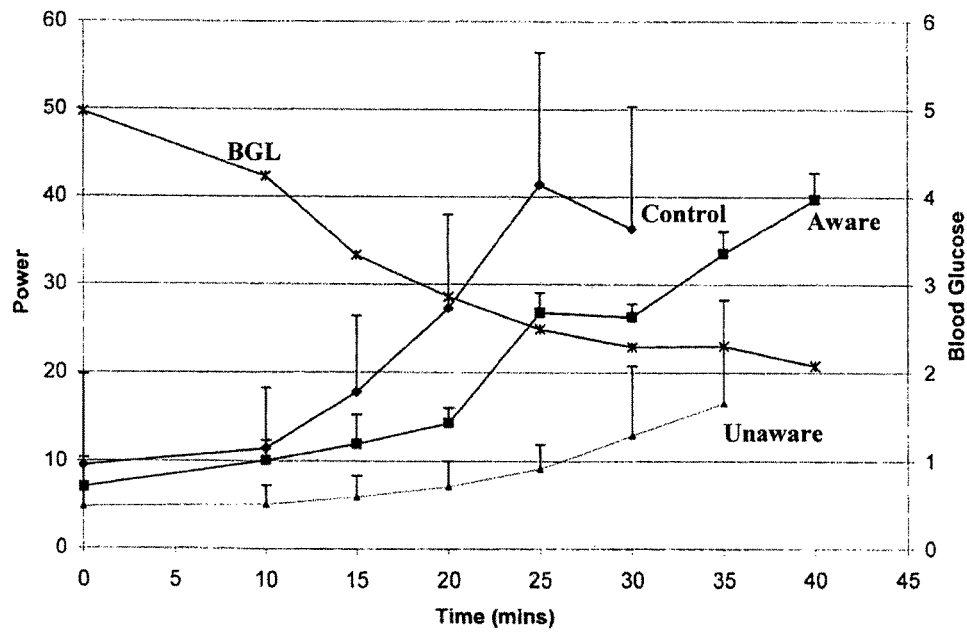
FIG. 4 provides a plot of Power (arm elevated) and BGL vs time for control, hypoglycaemic aware and hypoglycaemic unaware groups in a first study described herein.
Figure 5:
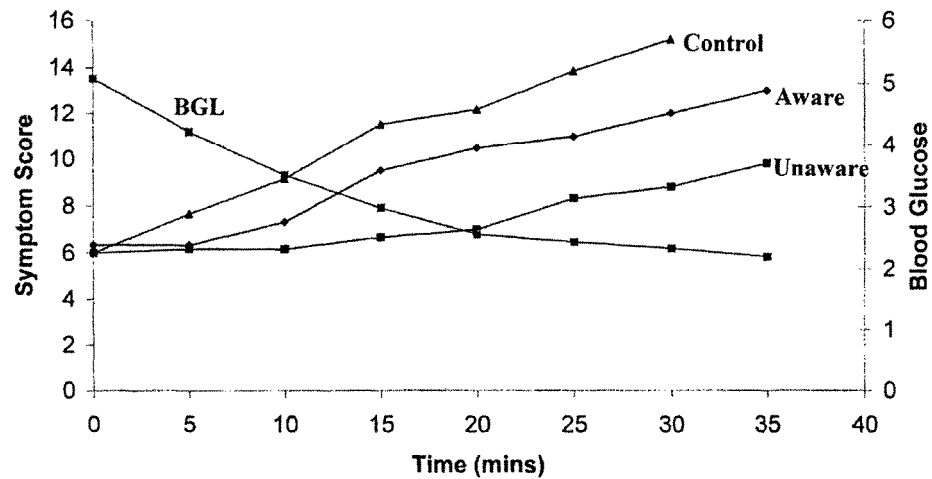
FIG. 5 provides a plot of Symptom Scores and BGL vs time for control, hypoglycaemic aware and hypoglycaemic unaware groups in a first study described herein.
Figure 6:
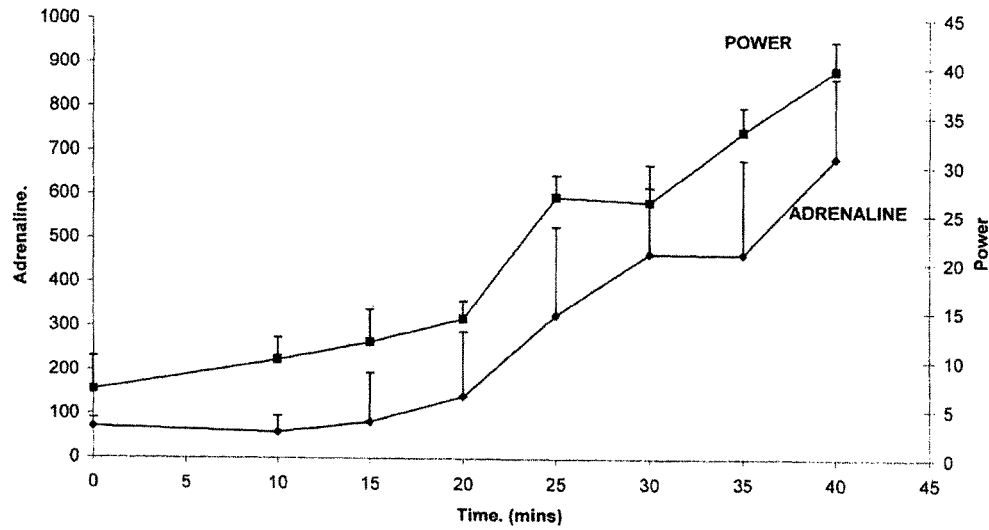
FIG. 6 provides a plot of Adrenaline and Power (arm elevated) as a function of time for the hypoglycaemic aware group in a first study described herein.
Figure 7:
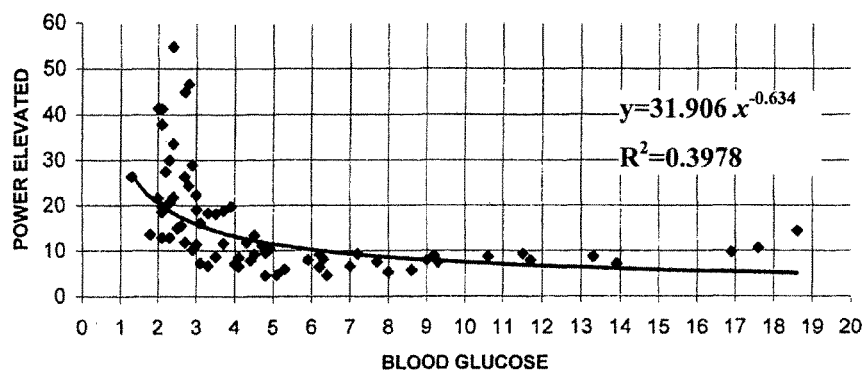
FIG. 7 is a plot of Power (arm elevated) vs BGL for the hypoglycaemic aware group in a first study described herein.
Figure 8:
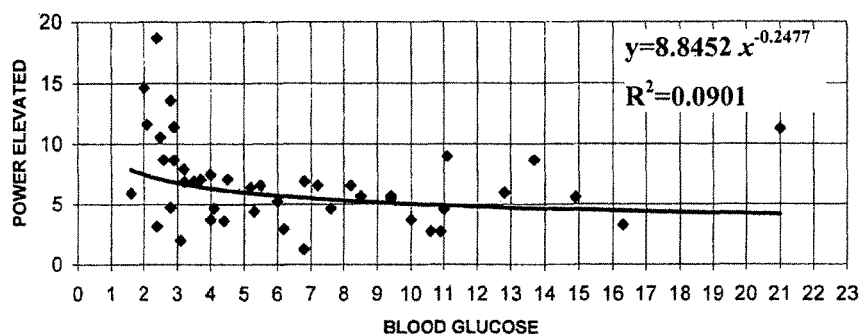
FIG. 8 provides a plot of Power (arm elevated) vs BGL for the hypoglycaemic unaware group in a first study described herein.

FIGS. 3, 4 and 5 are plots of Adrenaline, Power (arm elevate) and symptom scores (respectively), and BGL vs time for control, aware and unaware groups. FIG. 6 is a plot of Adrenaline and Power (arm elevated) as a function of time for the aware group showing a correlation between Adrenaline and Power (arm elevated). FIGS. 7 and 8 are plots of Power (arm elevated) vs BGL for aware and unaware groups respectively.

Tables 2 to 4 show the BGL at which >25% increase from basal values occur, Basal to Peak values and various correlation, respectively, for each of the three groups.

TABLE 2

BGL for a >25% increase from basal values for symptoms, power and adrenaline.

| | BGL(mmol) AWARE | BGL(mmol) UNAWARE | BGL(mmol) CONTROLS |
|---|---|---|---|
| Symptom Score | 3.5 | 4.1 | 4.1 |
| Power Arm Elevated | 3.66 | 3.0 | 2.3 |
| Power Arm Resting | 3.26 | 2.9 | 3.18 |
| Adrenaline | 3.0 | 2.7 | 2.66 |

TABLE 3

Basal to peak values(±sem). BGL at peak.

| | Basal | Peak | BGL | % Change | p |
|---|---|---|---|---|---|
| Aware | | | | | |
| Systolic BP | 132 ± 8 | 152 ± 7 | 2.8 | 15.9 | 0.01 |
| Diastolic BP | 67 ± 5 | 78.5 ± 6 | 2.8 | 17.6 | 0.23 |
| Heart Rate | 70.8 ± 2 | 94 ± 6 | 2.8 | 32.7 | 0.003 |
| Power Elevated | 9.2 ± 2.4 | 38.1 ± 6.1 | 2.8 | 310 | 0.0003 |
| Power Resting | 1.3 ± 0.5 | 12.4:12.5 | 2.7 | 790 | 0.02 |
| Adrenaline | 54.6 ± 11 | 572 ± 118 | 2.8 | 947.0 | 0.003 |
| Noradrenaline | 497 ± 83 | 743 ± 144 | 2.8 | 49.3 | 0.01 |
| Unaware | | | | | |
| Systolic BP | 129.8 ± 9 | 149.2 ± 4.8 | 2.7 | 14.9 | 0.01 |
| Diastolic BP | 71.6 ± 3.9 | 80.2 ± 2.9 | 2.7 | 12.0 | 0.03 |
| Heart Rate | 68 ± 5.6 | 79 ± 6.2 | 2.7 | 15.1 | 0.04 |
| Power Elevated | 2.3 ± 1.1 | 5.2 ± 1.6 | 2.7 | 138.0 | 0.041 |
| Power Resting | 1.18 ± 1 | 3.3 ± 1.5 | 2.6 | 210 | 0.02 |
| Adrenaline | 22 ± 36 | 133 ± 36 | 2.2 | 2248.0 | 0.01 |
| Noradrenaline | 348.8 ± 59 | 648 ± 62 | 2.1 | 100.1 | 0.004 |
| Controls | | | | | |
| Systolic BP | 127 ± 9.3 | 142 ± 6.1 | 2.9 | 12.1 | 0.0007 |
| Diastolic BP | 73 ± 2.3 | 86 ± 2.9 | 2.9 | 7.7 | 0.43 |
| Heart Rate | 68 ± 2.5 | 86 ± 2.9 | 2.9 | 32.0 | 0.04 |
| Power Elevated | 15.2 ± 4.4 | 26 ± 7.7 | 2.3 | 76.0 | 0.03 |
| Power Resting | 4.8 ± 1.8 | 7.72 ± 2.3 | 2.4 | 63.0 | 0.045 |
| Adrenaline | 29.3 ± 2.7 | 312.6 ± 141 | 2.2 | 966.0 | 0.05 |
| Noradrenaline | 437.9 ± 103 | 644 ± 129 | 2.1 | 47.1 | 0.001 |

TABLE 4

Correlations

| | Aware | Unaware | Controls |
|---|---|---|---|
| BGL vs Adrenaline | 0.0073 | 0.0072 | >0.0001 |
| Adrenaline vs Noradrenaline | 0.30923 | 0.089539 | 0.670308 |
| Adrenaline vs Symptoms | >0.0001 | 0.0053 | 0.0432 |
| Adrenaline vs Systolic BP | 0.0371 | 0.2532 | 0.233652 |
| Adrenaline vs Diastolic BP | 0.184995 | 0.208795 | 0.288869 |
| Adrenaline vs Pulse rate | 0.00006 | 0.000559 | 0.003278 |
| BGL vs Noradrenaline | 0.5834 | 0.0071 | 0.2843 |
| Noradrenaline vs Symptoms | 0.8182 | 0.0002 | 0.795 |
| Noradrenaline vs Systolic BP | 0.0009 | 0.004 | 0.03 |
| Noradrenaline vs Diastolic BP | 0.241008 | 0.342184 | 0.068969 |
| Noradrenaline vs Pulse Rate | 0.187766 | 0.909045 | 0.185293 |
| BGL vs Power Elevated | 0.00000 | 0.00000 | 0.03771 |
| Adrenaline vs Power Elevated | 0.00000 | 0.01128 | 0.04085 |
| Noradrenaline vs Power Elevated | 0.6611 | 0.003459 | 0.643245 |
| BGL vs Power Resting | 0.00004 | <0.0001 | 0.03771 |
| Adrenaline vs Power Resting | 0.002094 | 0.7934 | 0.006977 |
| Noradrenaline vs Power Resting | 0.921084 | 0.0034 | 0.686058 |

A number of conclusions were drawn from Study 1. The main conclusion from the first study is that there was a highly significant increase in power to hypoglycaemia with both arm elevated and resting, which correlates with the decrease in blood glucose levels. This change is more marked in the hypoglycaemic aware group. There was however, no change in the frequency of tremor with hypoglycaemia.

There was also a significant increase in the adrenaline levels in the aware and control group. The change was less in the unaware group which had a more marked increase in noradrenaline than the other two groups suggesting that this is the prime responder to hypoglycaemia in this group. This difference in catecholamine response is reflected in the physiological parameters with less of an increase in systolic BP and heart rate in the unaware group. There is a significant correlation in the catecholamines with BGL.

A second study was then performed with the aims of identifying in real time the muscle tremor response to hypoglycaemia and to verify the muscle tremor findings of the first study. This study was performed with 14 subjects, of which two were subsequently omitted (1 vasovagal, 1 failed recording), leaving a group of four hypoglycaemic aware and eight hypoglycaemic unaware subjects. Subjects were seated in a reclined position in a chair and a first accelerometer was taped on the index finger of their non-dominant hand, and a second accelerometer was placed on their wrist (radial tubercle of the non-dominant hand). The accelerometers were connected to a laptop computer and analysed by digitising the signal, band pass filtering the signal, Fourier transforming, and then measuring the power of the band pass filtered signal (units $(cm/s^2)^2$). Measurements were taken in a resting position and an elevated position. Symptom scores, pulse rate, blood pressure, and BGLs (both venous blood and finger prick) were also monitored.

BGL were controlled and lowered until BGL dropped to a value of between 2.4 and 2.8 mmol/l via a finger prick test, after which I/V glucose was administered to reverse hypoglycaemia. Samples were taken every 10 minutes until BGL reached approximately 5 mmol/l and 5 minutes thereafter until 40 minutes after reversal of hypoglycaemia. Table 5 provides information on the 12 subjects.

TABLE 5

Subjects in Study 2 (2 subjects removed from data. 1 vasovagal, 1 failed recording)

| Parameter | Aware (4) | Unaware(8) |
|---|---|---|
| Age yrs | 54.8 | 51.2 |
| Duration diabetes. Yrs | 12 | 32 |
| BMI | 27.7 | 27.4 |
| HbAlc | 8.7 | 8.5 |
| Insulin dose. U/24 hrs | 105 | 42 |

Figure 9:
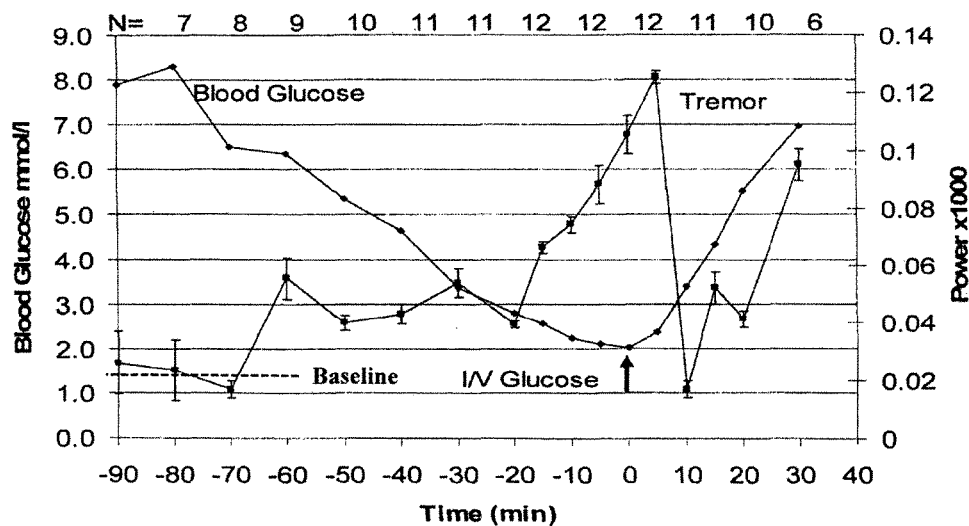
FIG. 9 provides a plot of BGL and Tremor (vertical wrist measurement) as a function of time in a second study described herein.
Figure 10:
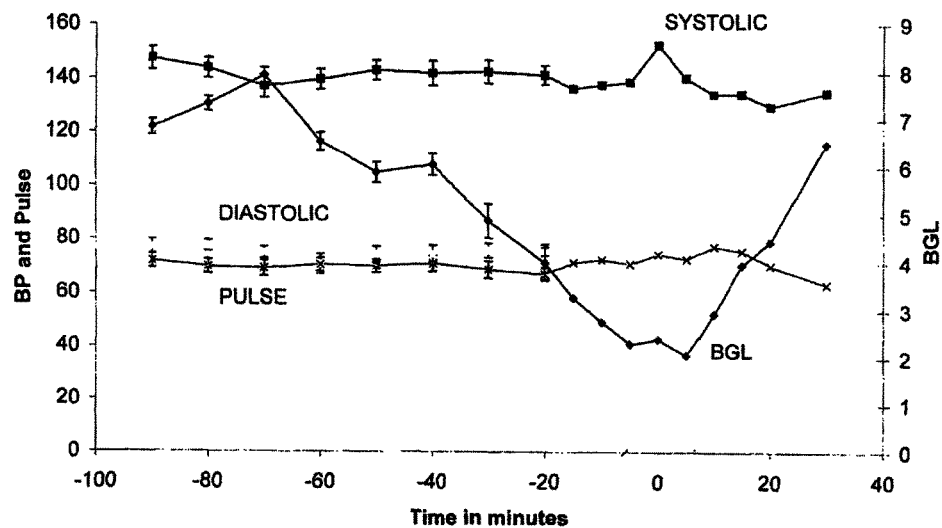
FIG. 10 is a plot of BGL, systolic and diastolic blood pressure as a function of time in a second study described herein.
Figure 11A:
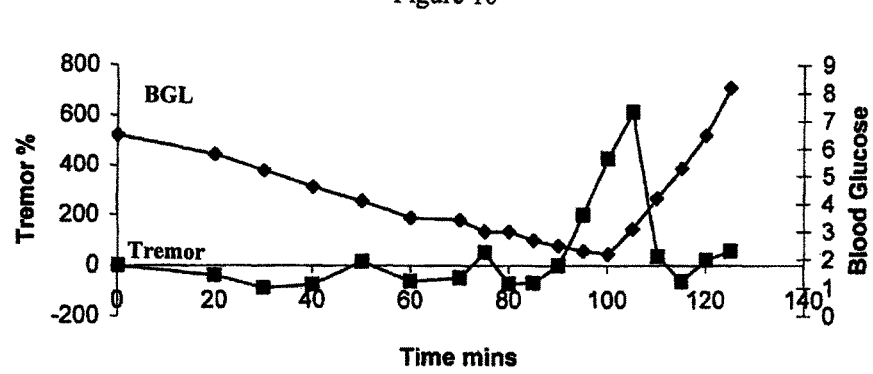
FIGS. 11A to 11I show individual plots of % change in tremor with respect to baseline and BGL vs time for nine patients (A to I) in the second study described herein.
Figure 11B:
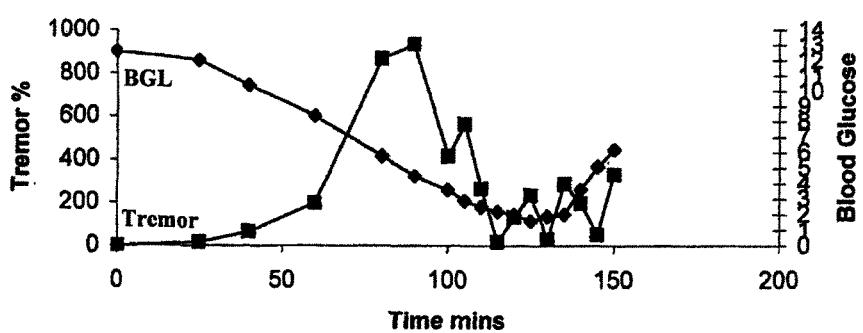
Figure 11C:
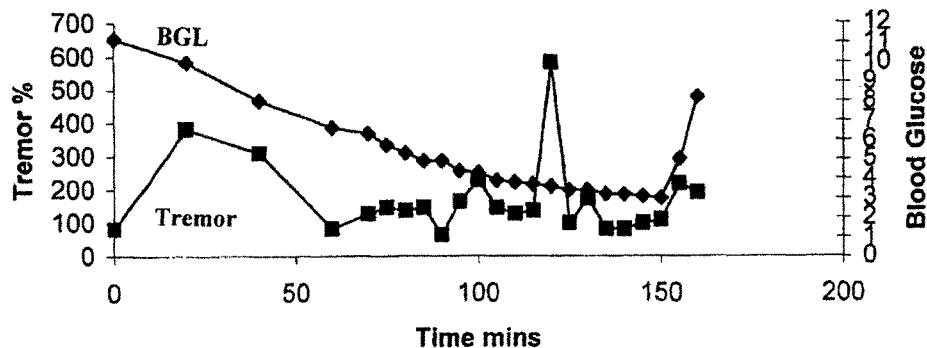
Figure 11D:
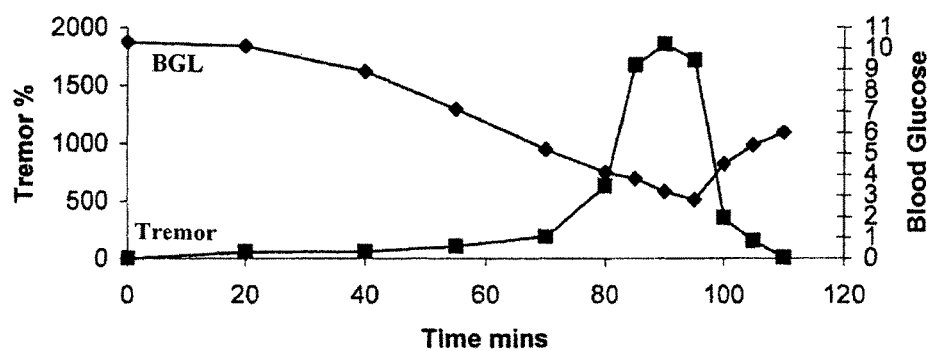
Figure 11E:
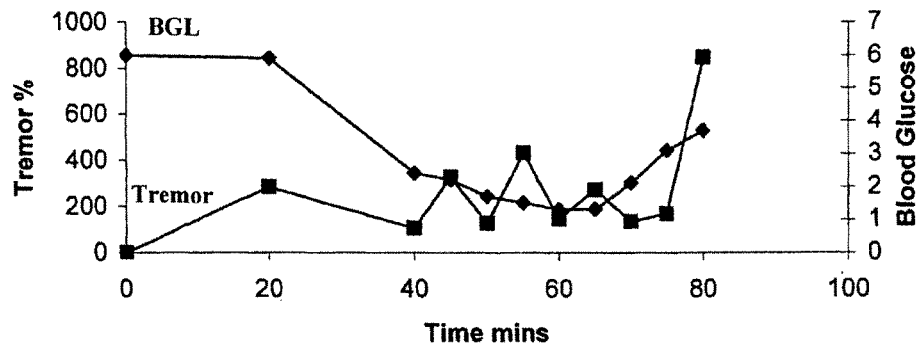
Figure 11F:
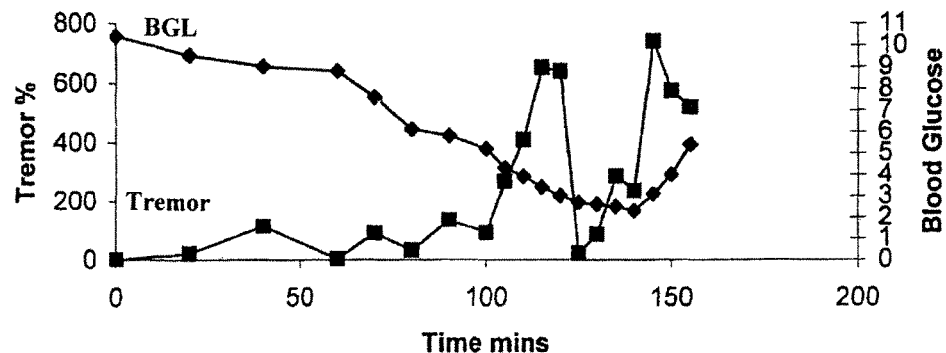
Figure 11G:
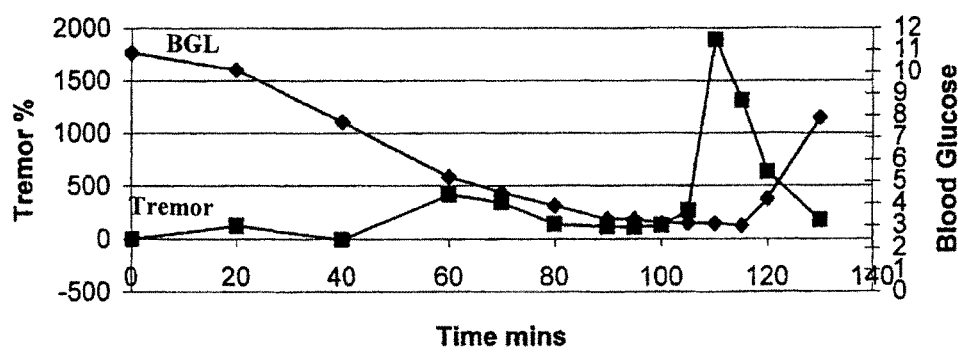
Figure 11H:
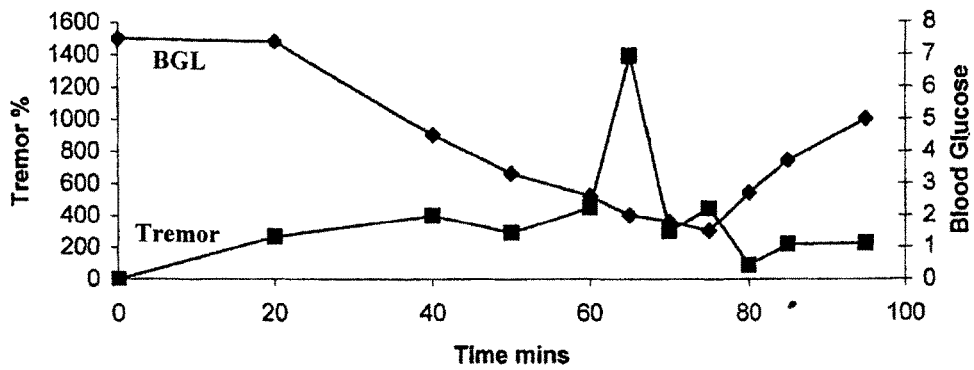
Figure 11I:
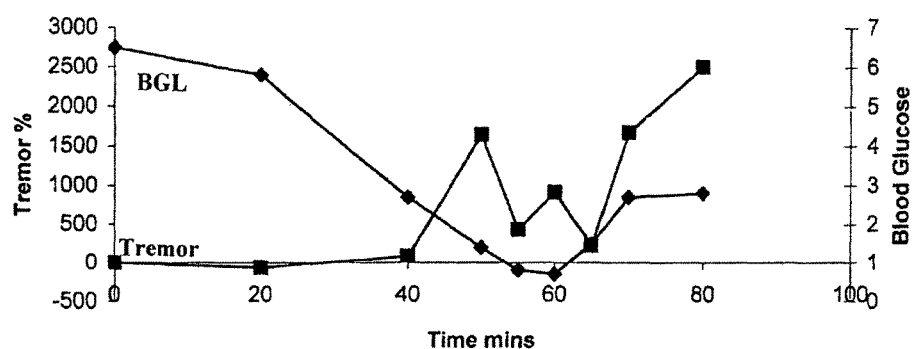

FIG. 9 is a plot of BGL and Tremor (vertical wrist measurement) as a function of time. FIG. 9 indicates a clear trend of increasing tremor power from the baseline as BGL decreases between about 6 and 3 mmol/l (corresponding to the onset of hypoglycaemia). A clear jump in power is also observable at a BGL of about 6.5. This increase in tremor is believed to correspond to a release of adrenaline in response to dropping BGL. As hypoglycaemia sets in (below about 3 mmol/l)l, there is an even sharper rise in tremor until UV Glucose is administered. FIG. 10 is a plot of BGL, systolic and diastolic blood pressure as a function of time, which indicates no significant change in blood pressure with dropping BGL. FIGS. 11A and 11I provide individual plots of the % change in tremor, in nine patients (A to I), with respect to baseline and BGL vs time.

To examine the change in wrist tremor as a function of time, a 3-segment regression model was tested. Based on plots of the data (individual and mean plots), there appeared to be 3 periods: one in which there was relatively little consistent change (segment 1); one in which there seemed to be an increase in tremor (segment 2); and one in which there was a decrease (segment 3). The same approach was used to examine the entire sample as a whole, as well as the aware and unaware groups.

Change in each segment was defined as linear with intercept and slope estimated separately. Time was the only predictor. The change points (the time at which the segments meet) were also estimated. Three equations were estimated:

$$\text{Segment 1: tremor} = \text{intercept}_1 + \text{slope}_1 \text{time} \quad (1)$$

$$\text{Segment 2: tremor} = \text{intercept}_2 + \text{slope}_2 \text{time} \quad (2)$$

$$\text{Segment 3: tremor} = \text{intercept}_3 + \text{slope}_3 \text{time} \quad (3)$$

The change points were estimated as well, with the restriction that the segments were continuous at the change points. Therefore, the change points were defined as:

$$\text{change\_point}_1 = \frac{(\text{intercept}_2 - \text{intercept}_1)}{\text{slope}_1 - \text{slope}_2} \quad (4)$$

$$\text{change\_point}_2 = \frac{(\text{intercept}_3 - \text{intercept}_2)}{\text{slope}_2 - \text{slope}_3}$$

Power resting at the wrist was also investigated. The results were divided from the time glucose was infused. This provided a fixed point in the study, as the timing of the blood glucose fall, rate of decrease and initial starting BGL varied from one subject to another. The time prior to the glucose infusion is given as negative, and the time after is positive. The study was divided into 3 phases, 40 minutes before glucose was infused (segment 2), all values preceding this time (segment 1) and results after glucose (segment 3). There was a significant relationship of blood glucose values to power (p=0.03) in this time period (segment 2). The increase in power for the group over the 40 minutes preceding glucose showed a suggestive but not statistically significant increase (p=0.08). Analysis between hypoglycaemic "aware" and "unaware" subjects showed that the increase in power in the aware group was close to significance (p=0.052). Although 11 of the 12 subjects showed a consistent increase in power it was not always within the 40 minute time frame used for analysis. There were also fluctuations in the level of the power values during this time (segment 2). The mean increase in power commenced 19 minutes prior to glucose infusion which correlates with a blood glucose value of 3 mmol/l, although there was subject variation. There was also a significant decrease in tremor following the infusion of glucose, which increased again as the BGLs increased. The time of the study was not taken out further to determine when the tremor returned to normal.

The main conclusion from Study 2 was that there was a significant correlation of tremor to BGL change (p=0.03). "Real time" recording identified changes in tremor. A high proportion of the subjects (66%) tested had hypoglycaemic unawareness. These subjects were the least able to mount a significant muscle tremor. It would be anticipated that other diabetic subjects who were either hypoglycaemic aware or had their diabetes for a shorter time would have a much greater tremor response.

Although statistical significance was not achieved in muscle tremor in the total group, in the "aware" group the significance in the increase in muscle tremor was (p=0.052). It is likely that with an increased number of subjects in the aware group (only 4 were included), the results would be likely to achieve statistical significance. There was no correlation between the duration of diabetes and wrist tremor. There were also non-significant changes in BP and pulse with hypoglycaemia in all groups. The decrease in muscle tremor at the nadir of the BGLs would suggest that a critical level of blood glucose is needed for muscle function, and that the return of the BGLs to normal restores the tremor (and muscle function), although the tremor remains until the adrenaline levels decrease. Awareness of hypoglycaemia is related to increased adrenaline levels which are decreased in the unaware group to hypoglycaemia. One subject had a major increase in muscle tremor and was "unaware".

The conclusions from the first and second studies indicate that the onset of hypoglycaemia could be predicted based upon measurements of physiological tremor. A third study was then conducted to identify and document changes in the physiological tremor (PT) of the forearm in healthy, non-diabetic subjects during usual daily living activities.

In this study, 10 non-diabetic subjects wore an accelerometer on the wrist which was connected to a data logger on the waist via a wire. The mean age was age 41 (range 13 to 67) and the mean weight was 76 kg (range 40-128 kg). No change in physiological tremor was detected with normal daily living. This included sleep, moderate exercise (2 bike riders), eating, house work and office work. Also, eight medical students (mean age 23.5) wore an accelerometer for 3 hours. No change in physiological tremor was observed for coffee drinking (instant, 1 or 2 teaspoons), tea drinking (1 or 2 tea bags), fasting overnight or carbohydrate intake (10 or 20 mls of cordial). The conclusion was that no changes were detected in physiological muscle tremor in non-diabetic subjects with normal living activities.

A fourth study was then conducted to measure changes in the physiological tremor of the forearm in type 1 diabetic subjects during routine daily living activities, along with the correlation with serum (tissue) glucose levels from a continuous glucose monitoring system.

In this study, 14 type 1 diabetes subjects were recruited along with 1 non-diabetic control, with each subject wearing an accelerometer on the wrist for a period of 2 or 3 days. The accelerometer was placed on the wrist (tubercle non-dominant hand) and connected to a ME6000 Data logger from Mega Electronics. Subjects performed daily living activities (ie allowing the wrist to be moving and resting) and hypoglycaemic events occurred spontaneously. Subjects kept a daily diary of activity and recognised hypoglycaemic events. No monitoring of pulse rate or blood pressure was performed. Finger prick BGL were taken by subjects, along with measurements of tissue glucose levels with a MiniMed Continuous Glucose Monitoring System. The Minimed records glucose levels at 5 minute intervals whilst the ME 6000 records data continuously. Data was logged (obtained) at 5 minute intervals at timing of blood glucose samples and analysed at the completion of the trial.

This was a very difficult study due to frequent breakdowns in blood glucose monitoring. The sensor had to be replaced in 6 subjects. Further, patient interference with the recorder was high with leads taken out, pins bent, and the unit switched on and off. The study had to be terminated early due to a patient wearing the accelerometer in the shower and shorting the data logger.

TABLE 7

Subjects in study 4 (data was only obtained on 6 patients)

| Subjects | 12 |
|---|---|
| Sex | M 6, F 6. |
| Age | 51 |
| Duration diabetes yrs | 26 |
| Weight kg | 84 |
| Hypos/week | 1 |
| Total insulin dose/day | 76 |
| BP | 127/76 |
| Medication | (N) |
| Anti Lipid | 6 |
| Antihypertensives | 5 |
| Aspirin | 4 |
| Antidepressives | 1 |
| Thyroxine | 3 |
| Others (calcium, omperidone) | 2 |

The mean power base line for subjects 1 to 5 was 12 with a range of 11 to 13. The mean absolute power increase above base line during onset of hypoglycaemia, defined as when BGL was between 4-5 mmol/l, was 19.46 (72% increase). This further increased to 20.66 (78.9% increase) as BGL dropped below 4 mmol/l corresponding to a hypoglycaemic event. As subject 6 was on Zoloft (a tranquiliser) they were analysed separately and had a mean power base line of 3.5. Spontaneous hypoglycaemia occurred but with a slow onset and took longer to recover. Further studies on persons with anti-depressants would need to be undertaken to better define the changes.

Figure 12:
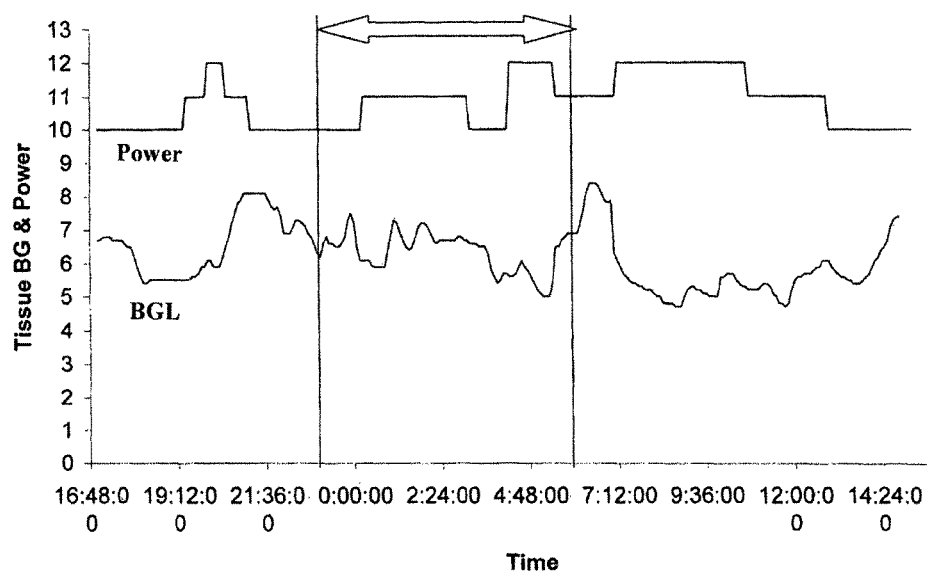
FIG. 12 shows a plot of power and BGL as a function of time for a control subject in study 4.
Figure 13:
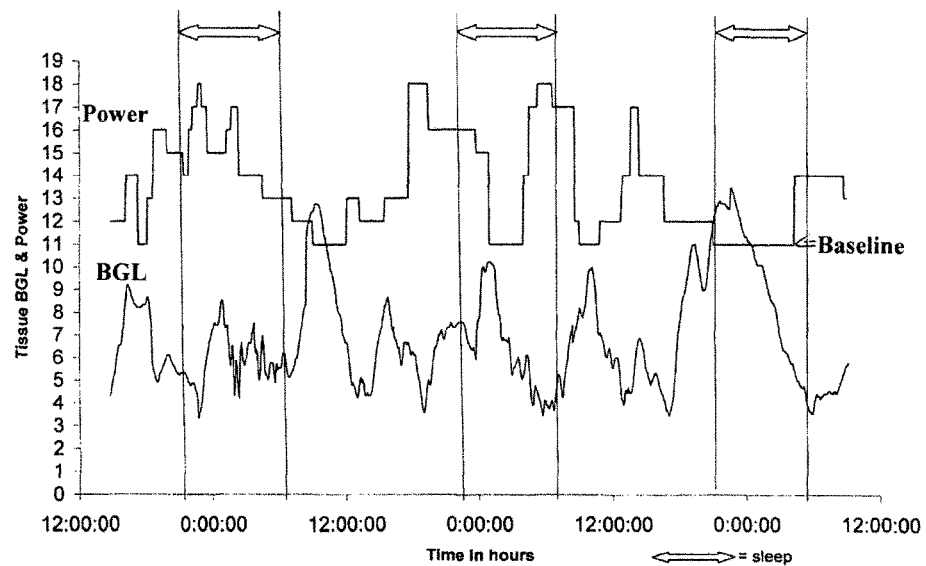
FIGS. 13 to 18 show plots of power and BGL as a function of time for six diabetic subjects in study 4.

FIG. 12 shows a plot of power and BGL as a function of time for a control subject in study 4. FIGS. 13 to 18 show plots of power and BGL as a function of time for 6 diabetic subjects in study 4. Measurements were obtained every 5 minutes by the data logger and digitised, band pass filtered, and Fourier Transformed to allow a measurement of power. These were then time averaged and plotted. All figures are annotated with sleeping periods designated by horizontal arrows.

Figure 14:
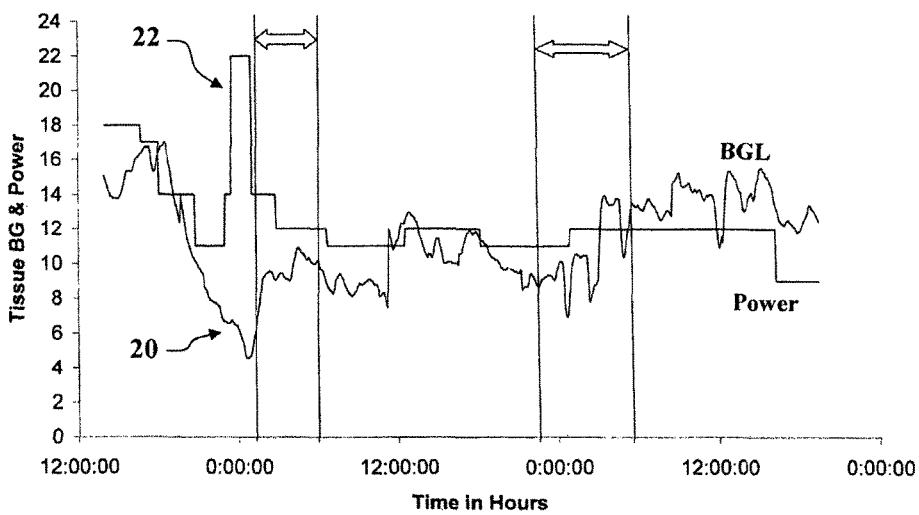
Figure 15:
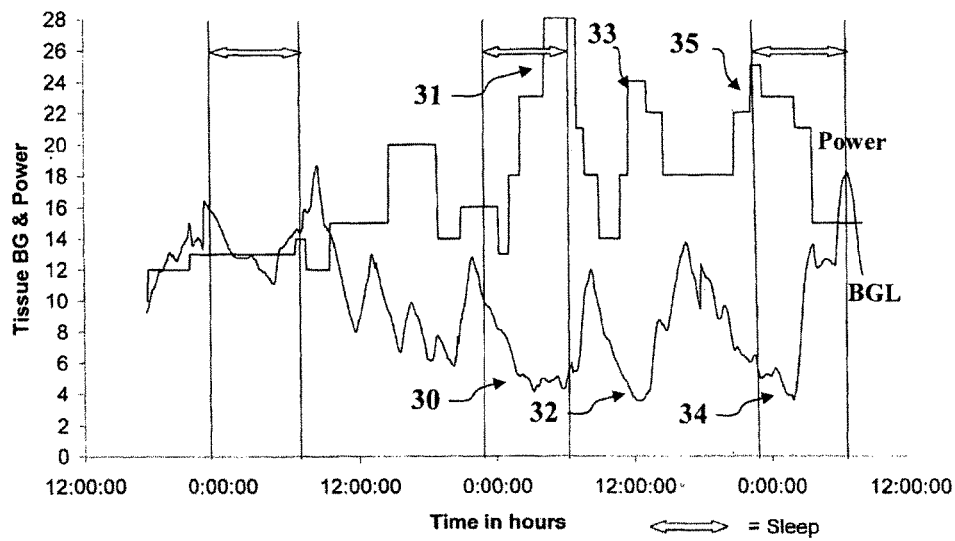
Figure 16:
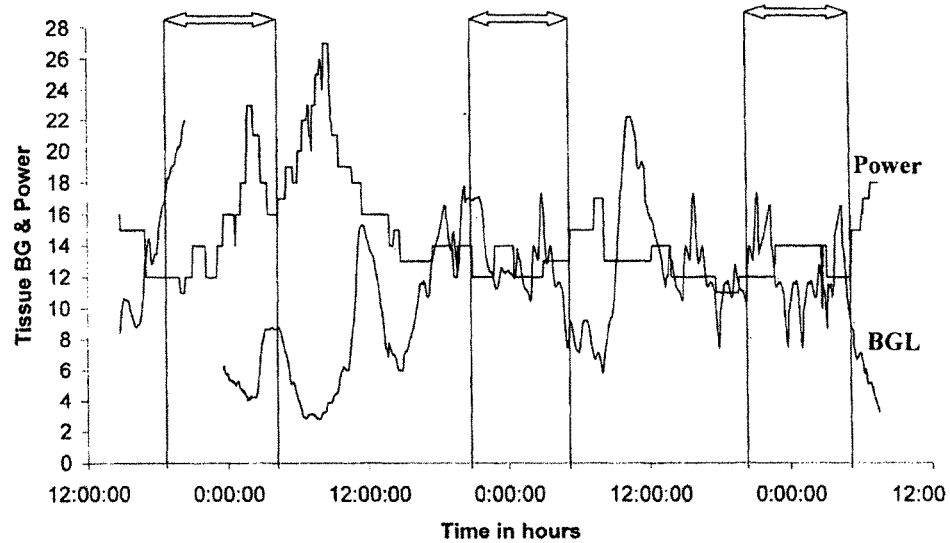
Figure 17:
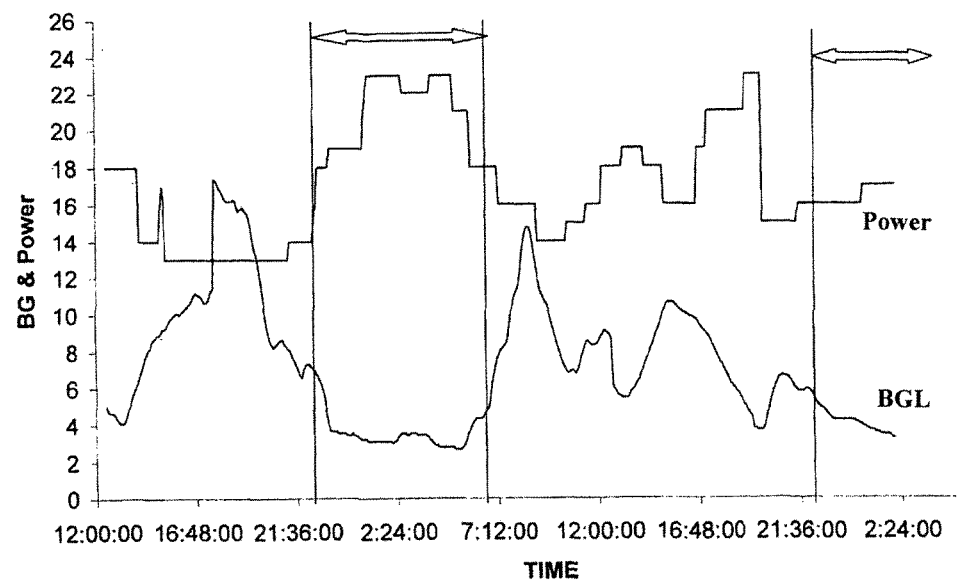
Figure 18:
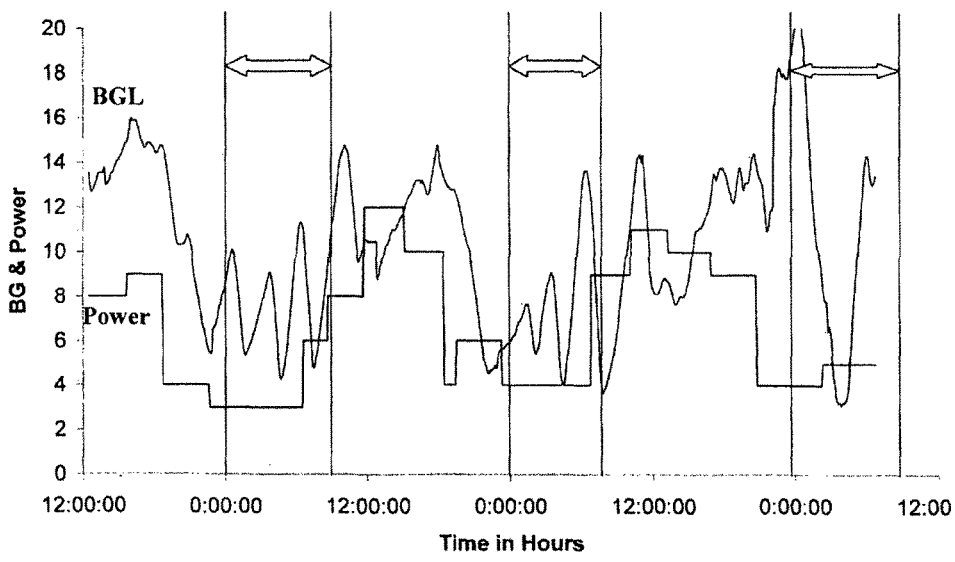

FIG. 12 shows that the baseline power was about 12 without significant variation. FIGS. 13 to 18 show that power measurements are significantly more varied in diabetic subjects. Further, these figures show the development of numerous hypoglycaemic events, both whilst awake and sleeping, in which power increases with decreasing BGL. For example, FIG. 14 shows an example of a hypoglycaemic event 20 occurring around midnight (0:00) on the first day, and clearly shows an increase in power 22. FIG. 15 also shows several hypoglycaemic events 30 32 34, both whilst awake and sleeping, in which power increases with decreasing BGL 31 33 35. Additionally, whilst hypoglycaemic events are shown, there are not corresponding false positives associated with normal day to day activities. FIG. 14 is of particular interest as the subject (subject 2) is a construction worker and engages in a range of physical activities.

A direct relationship between decrease in glucose levels and an increase in Power was observed in this study with a power increase of 72% above base line at a tissue glucose value between 4-5 mmol. Further the power increase was noted irrespective of whether the subjects were awake or asleep, or active or inactive.

The results of these four studies led to the conclusion that physiological tremor increases in amplitude and rate of increase with the onset of hypoglycaemia. Based on these results, an increase of 25% in power is detectable and could be used as a threshold amount for triggering an alarm to alert a user of a sensing apparatus. Further, these studies show that the change is detectable during normal day to day activities, and is not susceptible to false positives, thus making this approach reliable.

FIG. 1 outlines a method for detecting the onset of hypoglycaemia in a subject 100. The method includes receiving a physiological tremor signal from a portable sensor worn by a subject 110. The physiological tremor signal is then analysed over a first period of time 120. An alarm is then generated when a change in the physiological tremor signal indicative of the onset of hypoglycaemia in the user is detected 130.

Hypoglycaemia does not have a specifically defined range, but is generally considered as a blood glucose level (BGL) below about 3.5 mmol/l or 3 mmol/l. Similarly, the onset of hypoglycaemia is not an exact range, but approximately corresponds to a drop below about 5 mmol/l (or into the range 3-5 mmol/l). Detection of the onset may involve studying the signal at higher levels (eg 7-8 mmol/l) and examining decreases over time.

In one embodiment of the present invention, the sensor is an accelerometer which produces a continuous signal indicative of the amplitude and frequency of physiological tremor. Suitable accelerometers include piezoelectric, piezoresistive, capacitive based devices, micro electro-mechanical systems (MEMS), etc, which may be configured or are capable of detecting accelerations over a frequency range of 0-50 Hz and preferably in the 7-15 Hz range. For example, Measurement Specialties Incorporated produce a range of suitable piezoelectric accelerometers including the Model 3031 Accelerometer (circuit board mountable, range of ±50 g and a frequency response of 0-1000 Hz) and the Model 3022 Accelerometer (solder pads or pins, range of ±2 g and a frequency response from 0 to 150 Hz), Analysing the physiological tremor signal may include filtering to admit frequencies in a frequency range corresponding to physiological tremor. For example, a high pass filter could filter our frequencies above 50 Hz, or a band pass filter could be used which filters the signal to the 0-50 Hz range. The range of the band pass filter could be further selected based on the intended location that the sensor will be worn, or based on a user input indicating where the sensor is being worn. For example, a wrist worn sensor could apply a band pass filter with a range of 7-15 Hz or 8-12 Hz to limit signals to a particular bandwidth for that location.

An appropriate transform such as Fourier Transform (or a Discrete Fourier Transform) can be applied and the power spectrum of the signal calculated over the filtered range. Other transforms may be used including Hartley Transforms, wavelet transforms, short time Fourier transforms, etc, and discrete versions thereof. Windowing functions and other signal processing methods may also be used. Samples could be continuously collected, processed and stored over time to obtain a time series of power measurements (ie plurality of power measurements can be obtained). These power measurements can then be analysed to detect a change in the power measurement over some period of time (or time range) prior to the current measurement. For example, a sliding time window could be used. The measurements could be made continuously, or sampled at a certain rate such as 0.1 Hz, 1 Hz, 10 Hz, etc. Alternatively to save power, a group of samples could be taken periodically such as every minute, or every five minutes and used to obtain a power measurement. Samples could be combined and averaged either before or after calculation of the power spectrum measurements. Trend or regression analysis may be performed to assist in detecting a change in the power measurement signals, such as a gradual increase in power. The rate of change (ie derivative) of the power measurements could also be studied. Studying the rate of change, and detecting a point of inflection could be used to indicate that BGL is rapidly dropping. More complex analysis methods could also be performed in which the tremor signal is divided up into frequency ranges (Eg 0.5, 1, 2 Hz bins over the bandwidth) and power (or some other measure such as amplitude) in each range analysed. Similarly detection of the change could be based on analysing another quantity based upon (or a function of) the power measurements (eg square root of power, log of power, etc).

The tremor signal and/or power measurements can be measured in any appropriate units (eg $cm/s^2$, $(cm/s^2)^2$, $m/s^2$, $(m/s^2)^2$, g, $g^2$). The magnitude and units of the tremor signal and/or power measurements will depend upon factors such as type of sensor chosen and its sensitivity and location of the sensor, along with the signal processing performed such as the amount of amplification of the signal, filtering, windowing, averaging, etc. Irrespective of the measurement units used and absolute values the power measurements obtained from the sensor are analysed to determine changes in the measurements (or changes in the rate of change) and are thus insensitive to the choice of these factors. That is, by analysing the tremor signal (or power measurements) for a change such as with respect to a baseline, or the rate of change (i.e. derivative) of the tremor signal, the detection of onset of hypoglycaemia is insensitive to these factors. A calibration (or configuration) process can be performed to set, determine or compensate for any such factors for specific implementations, eg to select appropriate gains, filters, and thresholds for the specific sensor and intended location.

The signal may be studied to determine a change is relative to a predetermined baseline. The predetermined baseline may be predetermined for the user from a calibration process. For example a reading could be made at the same time as skin prick test, and the measured BGL entered into the device. This could be repeatedly performed over a period of several hours or days to calibrate the tremor signal (or power measurements) to the patient's actual BGL readings. Calibration could be performed when the user first obtains the device, or at another time. Calibration could also be continuous, in that each time a user performs a skin prick test (or other reading of BGL), they could have the option of storing the tremor signal and entering the corresponding BGL level. This would allow continuous adjustment of the thresholds. Alternatively the data could be stored or logged, and then analysed at a later time using a more powerful computing device which executes calibration or analysis modules. This analysis could be performed by a physician or carer. This external analysis process could be used estimate updated thresholds which can then in turn be downloaded into the device. Dynamic thresholds may also be used in which the dynamic threshold is determined from analysing the physiological tremor signal over an earlier time period. For example, the earlier time period could be several hours previously (eg 1, 2, 3, 4, 5, 6, 7, 8, 9, 10, 11, 12 hours earlier, or the previous hour (or several hours) on preceding days (eg 1, 2, 3, 4, 5, or more preceding days). The studies above indicate an increase of 25% in power is detectable and could be used as a threshold amount for triggering an alarm to alert a user of a sensing apparatus (or device). However other thresholds or measures based upon the increase in power associated with increased amplitude of the tremor signal and/or an increase in the rate of change of amplitude or power could also be used. The sensitivity of the system will vary based upon location (placement) of the sensor, and the choice of actual sensor. Accordingly other thresholds may be chosen based upon such factors. A threshold could be set as increase in power of 5%, 10%, 15%, 20%, 25%, 30%, 40%, 50%, or more with respect to a reference value. Alternatively the increase could be an increased rate of change of power (ie derivative of power). The reference value may be fixed reference such as preprogrammed, or determined based on physiological data of the patient (eg sex, age, height, weight, disease status, medications taken, etc) or it may be determined by a calibration process. The reference value may be a dynamic reference, taking into account past values, or other factors such as time of day or activity.

Figure 2A:
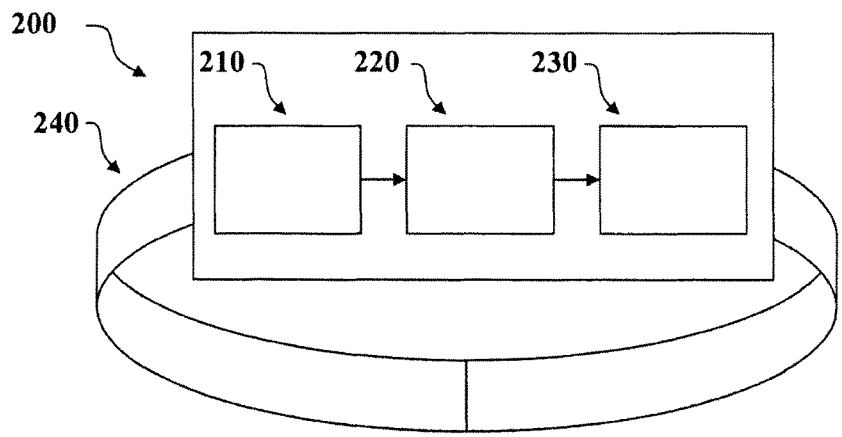
FIG. 2 provides a schematic diagram of a wearable apparatus for detecting the onset of hypoglycaemia in a subject according to an embodiment of the invention.

A portable wearable apparatus (or device) may be manufactured to perform measurements, analyse the signals and provide an alarm. FIG. 2 shows a wearable device 200 for detecting and alerting the user of the onset of hypoglycaemia according to an embodiment of the invention. The wearable apparatus 200 includes a sensor 210, an analysis module 220, an alarm 230 and an attachment means 240. The sensor may be an accelerometer for measuring physiological tremor in the subject (user). The analysis module, which may be provided in hardware, software, or a combination of the two, analyses the signal from the sensor over a period of time to detect a change in the tremor signal indicative of the onset of hypoglycaemia in the user. An alarm is provided for generating an alarm to alert the user when such a change is detected by the analysis module. An attachment means, such as a wrist strap, watch band, strips with matching Velcro® pads, buttons, studs, glue, suction pad, etc is also provided to allow the apparatus to be worn by the user. The apparatus can be worn on a wrist, ankle, waist, etc. The apparatus may be a distributed apparatus (or device) in which components are operatively coupled via wired or wireless links, and the individual components are worn or carried in different locations by a patient. The apparatus may include additional components such as a battery, time functionality, data port, communications interface, etc.

Figure 2B:
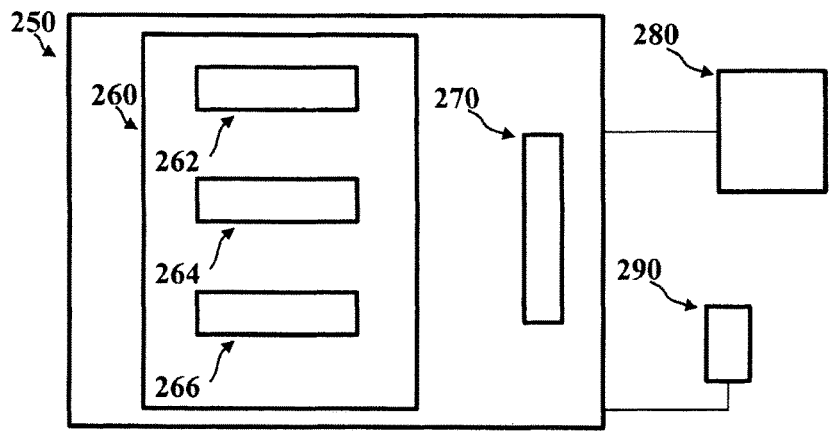

A computing apparatus 250 is illustrated in FIG. 2B and comprises a processing unit 260 such as a central processing unit CPU, microprocessor or microcontroller; a memory 270; one or more output devices 280 such as an alarm circuit and LCD display; and input devices 290 such as an accelerometer or tremor sensor, and user input buttons. The processing unit 260 may comprise an Input/Output Interface 262, an Arithmetic and Logic Unit (ALU) 264 and a Control Unit and Program Counter element 266 which is in communication with input and output devices (eg accelerometer or tremor sensor, user input buttons and alarm and display apparatus) through the Input/Output Interface. The Input/Output Interface may comprise a network interface and/or communications module for communicating with an equivalent communications module in a user input glove using a predefined communications protocol (e.g. Bluetooth, Zigbee, IEEE 802.15, IEEE 802.11, TCP/IP, UDP, IR protocols, etc). The memory is operatively coupled to the processor(s) and may comprise RAM and ROM components. The memory may be used to store the operating system and additional software modules and instructions that can be loaded and executed by the processor(s).

The computing apparatus (or device) may be a single computing or programmable device, or a distributed device comprising several devices, components or modules operatively connected via wired or wireless connections. Dividing the apparatus into separate components allows placement of the sensor at a desired location on the body, such as an arm or leg to increase sensitivity to the tremor signal, or to enable discrete placement of the sensor, and location of the analysis module and/or alarm module at separate locations, such as on the hip, wrist, or carried by the user in a pocket or handbag. In such a case, the components could communicate over wireless links such as using Bluetooth, Zigbee or other IEEE or propriety communication protocols. The analysis module could be provided as a single device or distributed over two or more component devices. Similarly, the alarm device could be integrated with the analysis module or provided as a distinct unit. The processor and analysis module could located and executing on a computing device such as a patient's mobile phone which executes connection and analysis modules for connecting with the sensor to download data and upload configuration settings, and analysing the downloaded data. The alarm circuit or module could be co-located with the analysis module, or it could be located in a separate component and the analysis module could generate an alarm message or signal which is sent to the device that generates the alarm such as a mobile or watch to alert the patient or other person.

Alarms may be visual alarms (eg flashing lights), audio alarms, a text message, or a combination. Different alarms could be generated based upon the change in tremor signal. For example as the power of the tremor signal increases (indicating dropping BGL), the frequency and/or volume of an audio alarm could be increased. Similarly the intensity and frequency of pulses sent to an LED (or other light) could be increased. The text in a text message could be progressively more forceful. A series of steps or ranges could be defined for power measurements (ie corresponding to BGL levels), with the option of setting a different alarm for each range. The range and associated alarms could be predetermined or configured by the user. Similarly if analysis of the rate of change indicates a rapid dropping of BGL (ie increasing rate of increase of power) a different alarm signal could be issued to indicate that rapid action should be taken.

In one embodiment, a sensor component could be worn on a finger or wrist, and further comprise a battery and wireless communications apparatus, such as Bluetooth transceiver. The analysis module could then be provided in a separate apparatus which could be worn on the belt or carried by the subject. Alternatively, the analysis module could be distributed with some functionality performed at the sensor (eg digitisation and/or filtering) and some performed in a separate apparatus (eg Fourier Transform, power spectrum calculations, trend or change monitoring). A separate alarm module could also be provided. In one embodiment, a Bluetooth headset could be paired to the analysis module, and when connected, be used to issue an alarm to the user's ear. A backup alarm could be provided in the analysis module. In one embodiment, the analysis module could be a software module running on the subject's mobile phone. The sensor could transmit the sensor signal, or a processed form of the sensor signal to a Bluetooth receiver in the subject's mobile phone. A software application could perform analysis of signal and alert the subject if a hypoglycaemic event is detected. Additionally, the application could utilise the communications capabilities of the mobile phone to send a short message or call a nominated person.

In one embodiment, the apparatus could be provided as a single wearable apparatus in the form of a ring (for a finger) or otherwise with a watch-like appearance. For example, the various components such as the accelerometer, signal processor and alarm could be packaged together on a single circuit board. Additionally, the apparatus could include a display and provide standard watch functions. Such an arrangement would provide a discreet measuring apparatus.

One class of devices which could be suitably modified are the Actiwatch range manufactured by Philips Respironics The Actiwatch devices are wearable data loggers designed for long term (eg weeks or months) sleep/wake or patient activity studies and include an accelerometer, data logger, battery and communications interface in a wearable, watch-like device. The Actiwatch range includes the Actiwatch 2 which is a basic data logger, the Actiwatch Spectrum which includes an LCD tine/date display and 3 colour light sensors, and the Actiwatch Score which includes an LCI) display and an alarm to prompt the wearer to enter a score between 0-15. The Actiwatch 2 and Actiwatch Spectrum use a solid state piezoelectric accelerometer capable of measuring accelerations in the 0.5-2 g range (0.025 g resolution) with a frequency range of 0.35 Hz to 7 Hz at a sample rate of 32 Hz. The Actiwatch Score uses a cantilever beam piezoelectric accelerometer suitable for measuring accelerations in the 0.5-2 g range over the range of 3 Hz to 11 Hz at a sample rate of 32 Hz. These devices could be suitably modified by incorporation of an analysis module for analysing the signal from the sensor over a period of time and generating an alarm (via an alarm module) when a change indicative of the onset of hypoglycaemia is detected. This could be in the form of a microprocessor and associated memory which is configured with appropriate instructions, or a dedicated signal processor may be configured with suitable instructions to perform the above analysis and generate an alarm. Alternatively, the analysis module could include an application specific integrated circuit (ASIC) or a digital signal processor (DSP) to perform the required processing such as filtering, transforming and comparison or time analysis.

The system detects the onset of hypoglycaemia and issues an alarm or other alert so as to enable appropriate action to be taken by the subject or carer. For example, upon the generation of an alarm, the subject can then perform a finger prick test (or other appropriate diagnostic test) to determine their blood sugar level. If the onset of hypoglycaemia is confirmed by this test, then the subject can take appropriate action such as consuming a sugar rich food so as to raise their blood glucose level.

The present invention may offer several advantages over the prior art. These include:

Wearability (and thus portability) and non-invasiveness. The apparatus contacts the user's skin (or sits over clothing) and requires no internal probes, access to interstitial fluids, or any other invasive or semi-invasive requirement.

Provides an early warning of hypoglycaemia. The system allows for the detection of hypoglycaemia at a point where intervention is relatively simple by taking, for example, a sugar drop or drinking fruit juice.

Non-intrusive. The apparatus could be relatively small and compact with the ability to be concealed under or within other devices. This would allow the user to use the apparatus without attracting attention from the public at large.

Continuous monitoring. Traditional monitoring is done using a finger-prick test three or more times daily. While this is a very accurate measurement, the subject's glucose level may vary unexpectedly between tests (eg due to unplanned physical activity, environmental factors). By continuously monitoring the user's condition, the apparatus provides a valuable backup to existing monitoring techniques.

Durability. The apparatus can be engineered to have a long lifetime between battery changes and servicing. Many devices for continuous monitoring suffer from very short battery lives, often of less than a week.

Simple to use. The apparatus is intended to be extremely simple to operate, either as an off-the-shelf purchase, or with minor calibration. This would make it suitable for monitoring of less capable patients by carers (eg children or the infirm).

Inexpensive and simple to produce. The basic components are relatively inexpensive and may be readily obtained from standard electronics suppliers.

Measures fundamental biological parameters. The apparatus measures a physiological condition that is an indirect consequence of hypoglycaemia, but which, can not be caused by external factors (eg temperature changes).

Improved treatment. The ability to reliability detect, and thus prevent the onset of hypoglycaemia for diabetics (and others) would enable users to more tightly control their blood glucose level without fear of accidentally inducing hypoglycaemia, and therefore reduce or prevent long term damage associated with poor control of blood sugar Those of skill in the art would understand that information and signals may be represented using any of a variety of technologies and techniques. For example, data, instructions, commands, information, signals, bits, symbols, and chips may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. For a hardware implementation, processing may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. Software modules, also known as computer programs, computer codes, or instructions, may contain a number a number of source code or object code segments or instructions, and may reside in any computer or processor readable medium such as a RAM memory, flash memory, ROM memory, EPROM memory, registers, hard disk, a removable disk, a CD-ROM, a DVD-ROM or any other form of computer or processor readable medium. In the alternative, the computer readable medium may be integral to the processor. The processor and the computer readable medium may reside in an ASIC or related device. The software codes may be stored in a memory unit and executed by a processor. The memory unit may be implemented within the processor or external to the processor, in which case it can be communicatively coupled to the processor via various means as is known in the art.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers. Similarly the terms apparatus and devices are to be considered synonymous, and a device may be considered as being comprised of multiple discrete components which are functionally connected.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. A method for alerting a subject of the onset of hypoglycaemia, the method including the steps of:
   i) affixing a portable sensor to a limb of a subject, wherein the portable sensor comprises an accelerometer;
   ii) receiving a physiological tremor signal from the portable sensor worn by the subject;
   iii) analysing the physiological tremor signal over a first period of time to determine the tremor signal power; and
   iv) generating an alarm at the location of the portable sensor based solely on detecting a change in the physiological tremor signal indicative of the onset of hypoglycaemia in the subject,
   wherein the onset of hypoglycaemia, prior to glucose administration, corresponds to a decrease in blood glucose level (BGL) into a range of 3-6.5 mmol/L, and the detected change in the physiological tremor signal is an increase in tremor signal power of at least 50% relative to a reference value.

2. The method of claim 1, wherein the reference value is a predetermined baseline.

3. The method of claim 2, wherein the predetermined baseline is predetermined for the subject from a calibration process.

4. The method of claim 1, wherein the reference value is a dynamic threshold determined from analysing the physiological tremor signal over a second period of time, the second period of time preceding the first period of time.

5. The method as claimed in claim 1, wherein the step of analysing the physiological tremor signal over a first period of time comprises:
   filtering the signal from the sensor;
   calculating the power spectrum of the signal at a plurality of time points in the first period of time to obtain a plurality of power measurements; and
   detecting a change in the plurality of power measurements over the first period of time.

6. The method of claim 5, wherein the change in the plurality of power measurements over the first period of time is an increase in power over time.

7. The method of claim 5, wherein the change in the plurality of power measurements over the first period of time is an increase in the rate of change of power over time.

8. The method of claim 5, wherein the filtering of the signal includes filtering signals outside of the range 0-50 Hz.

9. The method of claim 8, wherein the range is 7-15 Hz.

10. A wearable apparatus for detecting the onset of hypoglycaemia in a subject, the apparatus including:
a sensor for measuring physiological tremor in a subject;
an attachment means for attaching the apparatus to a limb of the subject, wherein the portable sensor comprises an accelerometer;
an analysis for analysing-a physiological tremor signal from the sensor over a first period of time to determine the tremor signal power, and generating an alarm signal via the output interface to initiate an alarm to alert the subject based solely on detecting a change in the physiological tremor signal indicative of the onset of hypoglycaemia in the subject,
wherein the analysis module generates an alarm signal to initiate an alarm at the location of the sensor to alert the subject of the onset of hypoglycaemia, prior to glucose administration, upon a decrease in blood glucose level (BGL), into a range of 3-6.5 mmol/L, and the change in the physiological tremor signal is an increase in tremor signal power of at least 50% relative to a reference value.

11. The apparatus of claim 10, wherein the reference value is a predetermined baseline stored in the analysis module.

12. The apparatus of claim 11, wherein the predetermined baseline is predetermined for the subject from a calibration process performed by the analysis module.

13. The apparatus of claim 10, wherein the reference value is a dynamic threshold determined from analysing the physiological tremor signal over a second period of time, the second period of time preceding the first period of time.

14. The apparatus of claim 10, wherein the analysis module is configured to:
i) filter the signal from the sensor;
ii) calculate the power spectrum of the signal at a plurality of time points in the first period of time to obtain a plurality of power measurements; and
iii) detect a change in the plurality of power measurements over the first period of time.

15. The apparatus of claim 14, wherein the change in the plurality of power measurements over the first period of time is an increase in power over time.

16. The apparatus of claim 14, wherein the change in the plurality of power measurements over the first period of time is an increase in the rate of change of power over time.

17. The apparatus of claim 14, wherein the filtering of the signal includes filtering signals outside of the range 0-50 Hz.

18. The apparatus of claim 17, wherein the range is 7-15 Hz.

19. The apparatus of claim 10, further comprising an alarm module wherein the alarm module receives the alarm signal fr and generates an alarm to alert the subject when a change in the physiological tremor signal indicative of the onset of hypoglycaemia in the subject is detected.

20. A non-transitory processor readable medium comprising processor readable instructions to cause a processor to perform a method for alerting a subject of the onset of hypoglycaemia, the method comprising
i) affixing a portable sensor to a limb of a subject, wherein the portable sensor comprises an accelerometer;
ii) receiving a physiological tremor signal from the portable sensor worn by the subject;
iii) analysing the physiological tremor signal over a first period of time to determine the tremor signal power; and
iv) generating an alarm at the location of the portable sensor based solely on detecting a change in the physiological tremor signal indicative of the onset of hypoglycaemia in the subject,
wherein the onset of hypoglycaemia, prior to glucose administration, corresponds to a decrease in blood glucose level (BGL), into a range of 3-6.5 mmol/L, and the detected change in the physiological tremor signal is an increase in tremor signal power of at least 50% relative to a reference value.

21. The processor readable medium of claim 20, wherein the reference value is a predetermined baseline.

22. The processor readable medium of claim 21, wherein the predetermined baseline is predetermined for the subject from a calibration process.

23. The processor readable medium of claim 20, wherein the reference value is a dynamic threshold determined from analysing the physiological tremor signal over a second period of time, the second period of time preceding the first period of time.

24. The processor readable medium of claim 20, wherein the step of analysing the physiological tremor signal over a first period of time comprises:
filtering the signal from the sensor;
calculating the power spectrum of the signal at a plurality of time points in the first period of time to obtain a plurality of power measurements; and
detecting a change in the plurality of power measurements over the first period of time.

25. The processor readable medium of claim 24, wherein the change in the plurality of power measurements over the first period of time is an increase in power over time.

26. The processor readable medium of claim 24, wherein the change in the plurality of power measurements over the first period of time is an increase in the rate of change of power over time.

27. The processor readable medium of claim 24, wherein the filtering of the signal includes filtering signals outside of the range 0-50 Hz.

28. The processor readable medium of claim 27, wherein the range is 7-15 Hz.

29. A wearable apparatus comprising:
a memory storing instructions for execution by a processor;
an attachment means for attaching the apparatus to a limb of the subject, wherein the portable sensor comprises an accelerometer; and
the processor operatively coupled to the memory, the processor configured to implement a method for alerting the subject of the onset of hypoglycaemia, the method comprising the steps of:
i) receiving a physiological tremor signal from a portable sensor worn by a subject;
ii) analysing the physiological tremor signal over a first period of time to determine the tremor signal power; and
iii) generating an alarm at the location of the sensor, based solely on detecting a change in the physiological tremor signal indicative of the onset of hypoglycaemia in the subject,
wherein the onset of hypoglycaemia, prior to glucose administration, corresponds to a decrease in blood glucose level (BGL) into a range of 3-6.5 mmol/L, and the detected change in the physiological tremor signal is an increase in tremor signal power of at least 50% relative to a reference value.

30. The wearable apparatus of claim 29, wherein the reference value is a predetermined baseline.

31. The wearable apparatus of claim 30, wherein the predetermined baseline is predetermined for the subject from a calibration process.

32. The wearable apparatus of claim 29, wherein the reference value is a dynamic threshold determined from analysing the physiological tremor signal over a second period of time, the second period of time preceding the first period of time.

33. The wearable apparatus of claim 29, wherein the step of analysing the physiological tremor signal over a first period of time comprises:

filtering the signal from the sensor;

calculating the power spectrum of the signal at a plurality of time points in the first period of time to obtain a plurality of power measurements; and detecting a change in the plurality of power measurements over the first period of time.

34. The wearable apparatus of claim 33, wherein the change in the plurality of power measurements over the first period of time is an increase in power over time.

35. The wearable apparatus of claim 33, wherein the change in the plurality of power measurements over the first period of time is an increase in the rate of change of power over time.

36. The wearable apparatus of claim 33, wherein the filtering of the signal includes filtering signals outside of the range 0-50 Hz.

37. The wearable apparatus of claim 36, wherein the range is 7-15 Hz.

* * * * *